United States Patent [19]

McNichols et al.

[11] Patent Number: 4,725,263

[45] Date of Patent: Feb. 16, 1988

[54] PROGRAMMABLE CONSTANT CURRENT SOURCE TRANSDERMAL DRUG DELIVERY SYSTEM

[75] Inventors: Larry A. McNichols; John d. Badzinski, both of Coon Rapids; Joseph B. Phipps, Plymouth; Gary A. Lattin, Forest Lake; Paul D. Sorenson, Blaine; Rama Padmanabhan, Arden Hills, all of Minn.

[73] Assignee: Medtronic, Inc., Minneapolis, Minn.

[21] Appl. No.: 891,081

[22] Filed: Jul. 31, 1986

[51] Int. Cl.$^4$ .............................................. A61N 1/30
[52] U.S. Cl. ..................................... 604/20; 128/798; 128/803
[58] Field of Search ...... 604/20; 128/419 R, 639–641, 128/783, 798, 799, 802, 803

[56] References Cited

U.S. PATENT DOCUMENTS

| | | | |
|---|---|---|---|
| 3,794,910 | 2/1974 | Ninke et al. | 324/30 R |
| 4,019,510 | 4/1977 | Ellis | 128/172.1 |
| 4,292,968 | 10/1981 | Ellis | 128/207.21 |
| 4,301,794 | 11/1981 | Tapper | 128/207.21 |
| 4,325,367 | 4/1982 | Tapper | 128/207.21 |
| 4,354,508 | 10/1982 | Murfitt et al. | 128/798 |
| 4,398,545 | 8/1983 | Wilson | 128/798 |
| 4,457,748 | 7/1984 | Lattin et al. | 604/20 |

Primary Examiner—Lee S. Cohen
Attorney, Agent, or Firm—Reed A. Duthler; Joseph F. Breimayer; John L. Rooney

[57] ABSTRACT

An iontophoresis device including a control module and a disposable electrode module. The control module includes a flexible printed circuit board carrying the battery and other electrical components. The control module is so configured that by trimming it along one of several labeled lines, various current levels may be selected. Trimming the control module provides a simple method for varying the dosage of the drug delivered by the iontophoresis device and simultaneously provides an easily readable visual indicator of the dosage level.

10 Claims, 6 Drawing Figures 4,725,263

PROGRAMMABLE CONSTANT CURRENT SOURCE TRANSDERMAL DRUG DELIVERY SYSTEM

BACKGROUND OF THE INVENTION

This invention relates generally to medical electrical current generators and in particular to iontophoresis devices.

The use of DC current to deliver drugs through the skin of a patient is an old and well known process. Iontophoresis devices typically include a battery and two electrodes coupled to the battery. One electrode typically contains a drug in its ionic form, the other electrode is typically moistened with saline solution or provided with some other ionic conductive medium. For example, such an iontophoresis device is illustrated in U.S. Pat. No. 4,325,367 issued to Tapper. Control of the dosage of the drug provided by such devices has typically been accomplished by control of the current flowing through the electrodes. Various systems for regulating current flow through iontophoresis devices are disclosed in U.S. Pat. Nos. 3,794,910, 4,292,968, 4,301,794, and 4,019,510.

SUMMARY OF THE INVENTION

The present invention comprises an iontophoresis device adapted to be worn by an individual patient. As such, it is desirable that the device be light and flexible. It is also highly desirable that the device be inexpensive to manufacture and easy to use. The present invention meets all of these requirements.

The device includes a control module and a disposable electrode module. The electrode module includes both an indifferent electrode and an active electrode containing the medicament to be administered. The control module is based upon a flexible circuit board, and employs a plurality of constant current diodes mounted to the flexible circuit board coupled between the battery and one of the electrodes. The constant current diodes regulate the current applied to the electrodes. The conductors on the flexible circuit board are arranged in a fashion such that each current path which includes one of the current limiting diodes passes close to the edge of the flexible circuit board. This allows the current applied to the electrodes to be regulated by the simple expedient of trimming the edge of the flexible circuit board, disconnecting one or more of the current limiting diodes. The control module is provided with visual indications on its outer surface indicating where such trimming is to be accomplished and what the dosage level associated with such trimming will be. The dosage setting is easily ascertainable on visual inspection of the device.

DETAILED DESCRIPTION OF THE INVENTION

Figure 1:
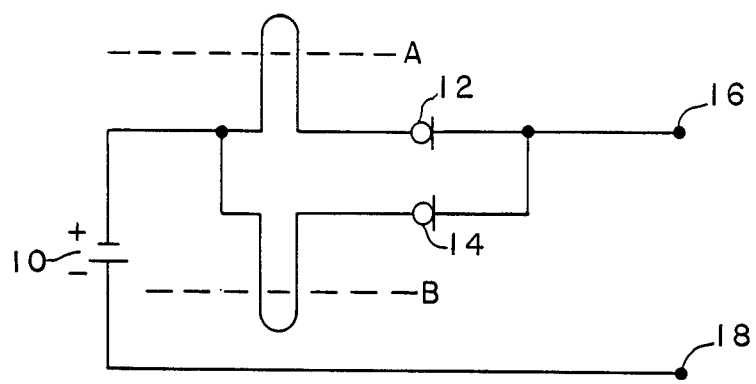
FIG. 1 is a schematic drawing of an embodiment of the invention in which three current levels are available.

FIG. 1 illustrates a schematic of an embodiment of the device providing three current levels. A DC current is provided by battery 10, and it is delivered via constant current diodes 12 and 14 to electrodes 16 and 18 which are the active and indifferent electrodes of the device. The choice of which electrode serves as the active or drug containing electrode, of course, depends upon the polarity of the ionic drug chosen.

The current delivered to electrodes 16 and 18 can be regulated by trimming the circuit paths connecting battery 10 to constant current diodes 12 and 14 along either dashed line A or dashed line B. Constant current diodes 12 and 14 may be chosen so that the current provided by diode 12 is twice that provided by diode 14. Therefore, if no current paths are trimmed, the current will be the sum of the currents through diodes 12 and 14. If the circuit paths are trimmed along line A or line B, the current provided will be one third or two thirds of full current, respectively.

Figure 2:
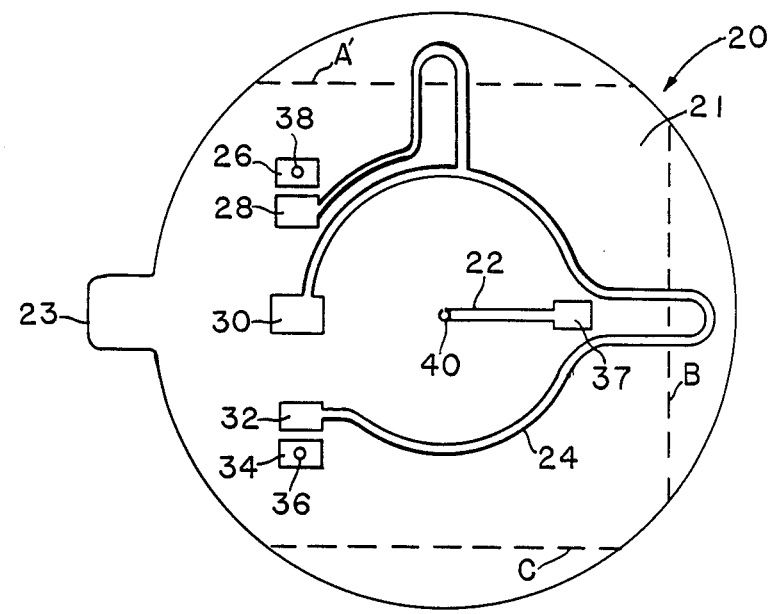
FIG. 2 is a plan view of the upper surface of the flexible circuit board embodying the schematic of FIG. 1.

FIG. 2 is a plan view of the top surface of a flexible printed circuit board embodying the schematic of FIG. 1. The circuit board 20 includes a flexible insulative, circular substrate 21 provided with metallized current paths 22 and 24 and connector pads 26, 28, 30, 32, 34 and 37. In use, a battery will be coupled between pads 30 and 37 with constant current diodes coupled between pads 26 and 28 and between pads 32 and 34. Pads 26 and 34 include small holes 36 and 38 which are plated through to make contact with the lower side of the printed circuit board. The small hole 40 at the end of current path 22 is also plated through to a conductive surface on the lower side of the circuit board. Trimming lines are illustrated at A', B' and C' for regulating current flow as discussed above in conjunction with the schematic illustrated in FIG. 1. Trimming line C' does not pass through any of the circuit paths, and serves only as a visual indicator that the highest current level available has been selected. This is believed to be a valuable feature because the same process is employed both to select any one of the three current levels, and to indicate the selected level.

Figure 3:
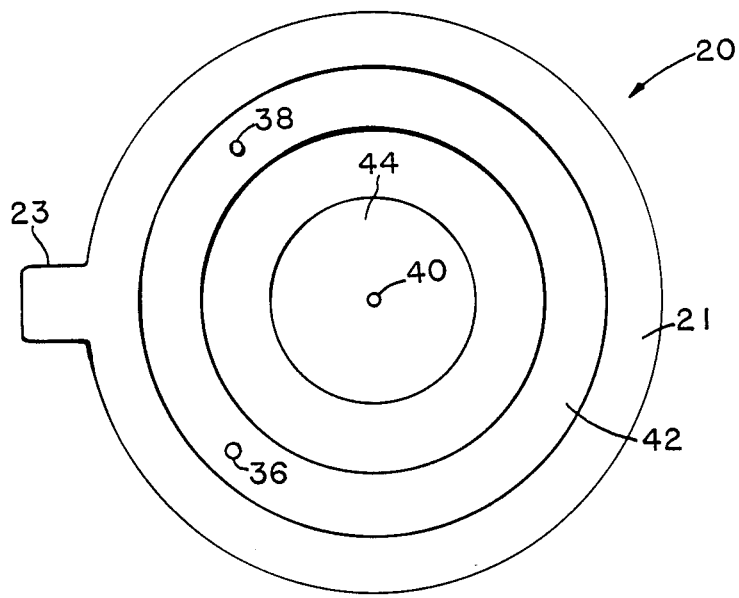
FIG. 3 is a plan view of the lower surface of the flexible circuit board illustrated in FIG. 2.

FIG. 3 shows the lower surface of the printed circuit board 20 illustrated in FIG. 2. Flexible substrate 21 includes two conductive areas 42 and 44. The plating through holes 36 and 38 couples circular conductive area 42 to pads 34 and 26 (FIG. 2). The plating through hole 40 couples current path 22 (FIG. 2) to the circular central conductive area 44. Conductive areas 42 and 44 are used to make contact with the electrodes of the disposable electrode module discussed below. Tab 23 assists in removal of the control module from the electrode module, as discussed below.

Figure 4:
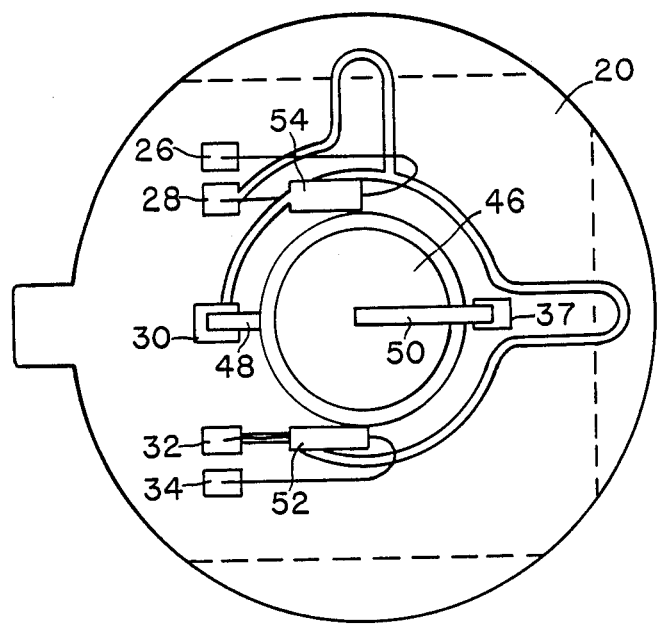
FIG. 4 is a plan view of the circuit board of FIG. 3 after mounting of electrical components.

FIG. 4 shows the upper surface of the flexible circuit board 20 of FIG. 2 with battery and current limiting diodes attached. Battery 46, which is preferably a button cell, is coupled to pads 30 and 37 by means of thin metallic straps 48 and 50 which have been tack welded to the positive and negative poles of battery 46, respectively. Constant current diodes 52 and 54 are mounted to pads 26, 28, 32 and 34, completing the circuitry.

Figure 5:
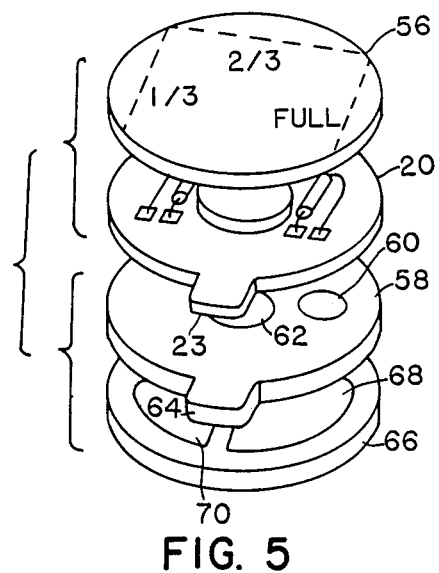
FIG. 5 is an exploded view of the various elements of the iontophoresis device including both the control module and the disposable electrode module.

FIG. 5 shows an exploded view of the various components of the iontophoresis device including both the control module and the disposable electrode module. In this view, flexible circuit board 20 can be seen with components attached. A flexible insulative backing sheet 56 is adhesively attached to the upper surface of flexible circuit board 20 and protects the components mounted thereon. Backing layer 56 has trimming lines marked thereon, along with an indication of the dosage level. The dosage level indicators may be as illustrated or may alternately be a specific indication of the amount of current or drug to be delivered.

Immediately below flexible circuit board 20 is the upper layer 58 of the disposable electrode module. This layer is preferably manufactured of a closed cell plastic foam. The layer includes two conductive members 60 and 62 which are so spaced that they contact the conductive areas 42 and 44 on the lower side of flexible circuit board 20, respectively. Because conductive areas 42 and 44 of flexible circuit board 20 are rotationally symmetrical, orientation of flexible circuit board 20 with respect to upper layer 58 is not critical. The upper surface of layer 58 is preferably provided with an adhesive to couple it to the lower surface of flexible circuit board 20, and to hold conductive feedthrough members 60 and 62 against the lower surface of flexible circuit board 20. Member 58 is provided with a tab 64 which, in conjunction with the tab 23 on flexible circuit board 20, allows for removal of the electrode module from the control module after use.

Located immediately below upper member 58 is lower member 66 of the electrode module. Member 66 is also preferably fabricated of a closed cell plastic foam, and includes two iontophoretic electrode inserts 68 and 70 which are preferably hydrophilic gel electrodes, at least one of which is provided with the ionic drug to be administered. The lower face of member 66 is provided with an adhesive to couple the assembled iontophoresis device to the skin. Electrodes 68 and 70 are preferably manufactured of a polar, non-ionic hydrophilic polymer gel through which the ionic drug is free to migrate. Whichever of electrodes 68 and 70 serves as the indifferent electrode is preferably impregnated with sodium chloride or other biologically compatible salt. Suitable electrode materials are discussed in European patent application publication No. 0 060 451 for an Iontophoretic Electrode, by Spevak et al, incorporated herein by reference in its entirety. The present invention is, however, believed to be appropriate for use with any of the various solid or gel iontophoretic electrode formulations presently available. As assembled, the iontophoresis device is preferably sufficiently flexible to conform to the contours of the human body.

Figure 6:
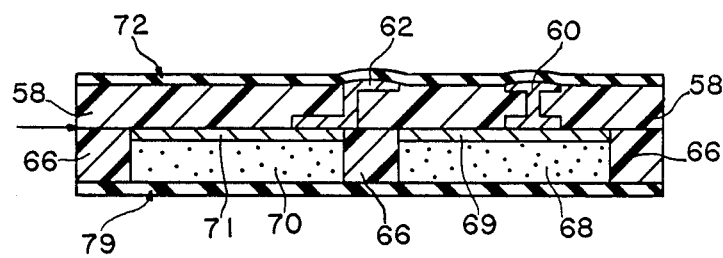
FIG. 6 is a cross-sectional view of the disposable electrode module.

FIG. 6 is a cross-sectional diagram of the disposable electrode module of the iontophoresis device. In cross section, it can be seen that conductive feedthrough members 60 and 62 extend through the thickness of upper member 58 and are coupled to metallic current distribution members 69 and 71 which in turn are coupled to electrodes 70 and 68, respectively. In cross section, it can be seen that feedthrough members 60 and 62 protrude slightly from upper member 58 to assure good contact with conductive areas 42 and 44 (FIG. 3). As provided for use, the electrode module would typically include release liners 72 and 74 protecting the adhesive which coats the upper face of member 58 and the lower face of member 66, respectively, as well as preventing electrodes 68 and 70 from drying out prior to use. In use, the control module is first trimmed to select the appropriate current level by cutting through the entire device along the selected line indicated on protective backing layer 56 (FIG. 5) with a scissors. Release liner 72 is then removed, and the electrode module is pressed against the lower surface of flexible circuit 20 connecting electrodes 68 and 70 to the control module. Release liner 74 may then be removed and the assembled iontophoretic device applied to the skin of the patient completing the electrical circuit and initiating drug delivery.

In the event that the initially selected dosage level proves to be unacceptably high, the physician may subsequently reduce the dosage level by further trimming the control module. In the illustrated embodiment, this allows the physician to reduce the dosage only if the full initial dosage was selected. However, in embodiments employing three or more constant current limiting diodes, several sequential reductions in dosage would be available to the physician if necessary.

Although the disclosed embodiment accomplishes current regulation using constant current diodes, use of other current regulating components or circuitry is believed to be within the scope of this invention.

In conjunction with the above written specification and drawings, we claim:

1. A control module for use in an iontophoresis device, comprising:
   a source of electrical current;
   connector means for electrically coupling said control module to active and indifferent electrodes of said iontophoresis device; and
   generally planar insulative substrate having an outer edge and having at least two parallel circuit paths, said circuit paths each coupling said current source to said connector means, said circuit paths each extending toward said outer edge of said substrate at locations spaced from one another, whereby a portion of said substrate adjacent said outer edge of said substrate may be trimmed to remove a portion of one of said circuit paths, and thereby interrupt said circuit path without interrupting others of said circuit paths.

2. A control module according to claim 1 wherein said substrate comprises a flexible printed circuit trimmable by use of a scissors.

3. A control module according to claim 1 or claim 2 wherein said substrate is further provided with visual indicator means for indicating appropriate paths for trimming said control module to interrupt circuit paths.

4. A control module according to claim 3 wherein said visual indicator means further indicate the resultant current leve achieved trimming through said substrate.

5. An iontophoresis device comprising a control module and an electrode moldule, wherein said electrode module comprises active and indifferent electrodes and first connector means for electrically coupling said active and indifferent electrodes to said control module and wherein said control module comprises a source of electrical current, second connector means for electrically coupling said control module to said active and indifferent electrodes and a generally planar insulative substrate having an outer edge and having at least two parallel circuit paths, said circuit paths each coupling said current source to said second connector means, said circuit paths each extending toward said outer edge of said substrate at locations spaced from one another, whereby a portion of said substrate adjacent said outer edge of said substrate may be trimmed to remove a portion of one of said circuit paths, and thereby interrupt said circuit paths without interrupting others of said circuit paths.

6. An iontophoresis device according to claim 5 wherein said substrate comprises a flexible printed circuit trimmable by use of scissors.

7. An iontophoresis device according to claim 6 wherein said electrode module is removably attached to said control module.

8. An iontophoresis device according to claim 5 or claim 6 or claim 7 wherein said control module and said electrode module are both sufficiently pliant to conform to the contours of a human body.

9. A method for adjusting current level in an iontophoresis device having an outer edge and comprising a current source, at least two electrodes, and a substrate having at least two parallel current delivery circuit paths extending from said current source to said first and second electrodes, each of said circuit paths extending near said outer edge of said iontophoresis device, spaced from each of the others of said circuit paths, said method comprising:

determining the desired current level for said iontophoresis device;

trimming away a portion of said iontophoresis device adjacent the periphery of said device to disconnect one or more of said circuit paths; and applying said trimmed iontophoresis device to the body of a patient.

10. A method according to claim 9 wherein said iontophoresis device comprises a control module including said at least two circuit paths and further comprises an electrode module, wherein said method further comprises the step of coupling said electrode module to said control module after said trimming step and prior to said applying step.

* * * * *